United States Patent [19]
Cox

[11] Patent Number: 5,213,563
[45] Date of Patent: May 25, 1993

[54] APPARATUS FOR OBTAINING AN ARTIFICIAL ERECTION

[76] Inventor: Allan J. Cox, 6 Seale Close, Beecroft, New South Wales, 2119, Australia

[21] Appl. No.: 829,765

[22] Filed: Jan. 31, 1992

[30] Foreign Application Priority Data

Feb. 4, 1991 [AU] Australia ............................. PK4445

[51] Int. Cl.⁵ .............................................. A61F 5/41
[52] U.S. Cl. ................................................. 600/38
[58] Field of Search ............................... 600/38, 39, 41

[56] References Cited

U.S. PATENT DOCUMENTS

| | | | |
|---|---|---|---|
| 2,874,698 | 2/1959 | Sell | 600/38 |
| 3,820,533 | 6/1974 | Jones | 600/38 |
| 4,378,008 | 3/1983 | Osbon | 600/38 |
| 4,718,411 | 1/1988 | Stewart | 600/38 |
| 4,741,329 | 5/1988 | Marcune | 600/41 |
| 4,753,227 | 6/1988 | Yanuck | 600/41 |
| 4,856,498 | 8/1989 | Osbon | 600/38 |
| 4,856,499 | 8/1989 | Kelly | 600/38 |
| 5,020,522 | 6/1991 | Stewart | 600/38 |

FOREIGN PATENT DOCUMENTS 87304239.4 5/1987 European Pat. Off. .

*Primary Examiner*—Cary E. O'Connor
*Attorney, Agent, or Firm*—Hamilton, Brook, Smith & Reynolds

[57] ABSTRACT

An apparatus for obtaining an artificial erection of the male genital organ including an elongate, generally tubular, body partially defining a vacuum changer adapted to accommodate the organ in a distended condition, the tubular body having an opening at one end to receive the organ and a substantially continuous peripheral rim adjacent the opening to seal the vacuum chamber around the organ, the other end of the body being substantially closed and including a manually operable pump adapted selectively and progressively to evacuate the vacuum chamber such that, in use, the resultant differential pressure causes blood to flow into the organ and induce an artificial erection.

3 Claims, 3 Drawing Sheets

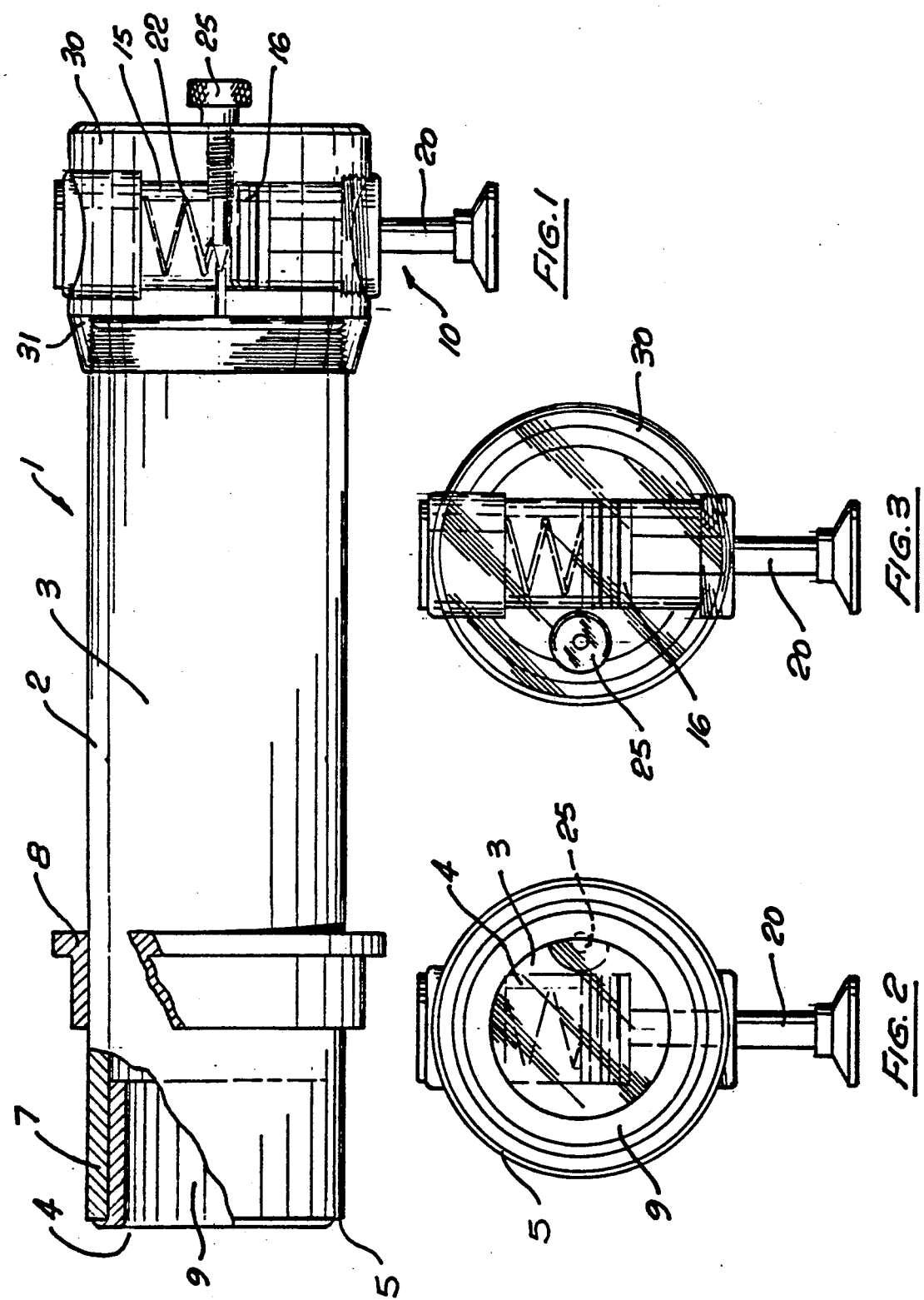

APPARATUS FOR OBTAINING AN ARTIFICIAL ERECTION

BACKGROUND OF THE INVENTION

The present invention relates to an externally applied apparatus for obtaining an artificial erection of the male genital organ.

In the past, various devices have been developed to artificially produce an erection by inducing blood flow into the genital organ. Such devices generally include a hollow tube to accommodate the organ and means to create a partial vacuum within the tube. The resultant differential pressure then causes blood to flow into the organ and produce the erection. Upon removal of the tube, the erection is maintained by an elastic band or other means.

However, these devices in practice have tended to be complicated arrangements which are difficult to use, overly artificial, inordinately large in size, or generally awkward and cumbersome. Moreover, most such devices are not self-contained, and require external sources of vacuum pressure.

It is therefore an object of the present invention to provide an improved erection aid device which overcomes or substantially ameliorates at least some of the deficiencies of the prior art, or at least provides a viable alternative.

SUMMARY OF THE INVENTION

Accordingly, the invention provides an apparatus for obtaining an artificial erection of the male genital organ, said apparatus including an elongate generally tubular body partially defining a vacuum chamber adapted to accommodate said organ in a distended condition, said tubular body having an opening at one end to receive the organ and a substantially continuous peripheral rim adjacent said opening to substantially seal the vacuum chamber around the organ, the other end of the body being substantially closed and including manually operable pump means adapted selectively and progressively to evacuate said vacuum chamber such that, in use, the resultant differential pressure causes blood to flow into the organ and induce an artificial erection.

Preferably, the pump means comprises a pressure cylinder, a piston manually reciprocable within the cylinder, and a cooperating pair of pressure actuable one-way valves respectively associated with the cylinder and piston, the valves being disposed such that axial displacement of the piston in a first direction corresponding to a suction stroke of the pump draws a corresponding volume of air into the cylinder from within the vacuum chamber, and displacement of the piston in the opposite direction in a return stroke exhausts the air from within the cylinder past the piston while isolating the vacuum chamber. The pumping cycle is thus repeated until the chamber has been evacuated to the required vacuum pressure.

Preferably, the piston includes a manually operable plunger protruding outwardly from the cylinder, and resilient bias means in the form of a spring disposed to urge the piston toward a rest position corresponding to the end of the suction stroke. In this preferred configuration, each suction stroke is effected automatically by the spring, and each return or exhaust stroke is effected manually by the plunger, against the bias force of the spring, such that the maximum extend to which the vacuum chamber is evacuated tends to be limited by the maximum bias force of the spring.

In one preferred embodiment, the pump is housed within an end closure element releasably and sealingly engageable with a corresponding end portion of the tubular body so as to define an end wall of the vacuum chamber, such that the pump is effectively integral with the assembled apparatus. The piston and cylinder axes preferably extend transversely with respect to the longitudinal axis of the body of the apparatus to facilitate single handed manual operation of the pump.

Preferably also, the apparatus includes a selectively operable pressure relief valve to vent the vacuum chamber to atmosphere and thereby release the apparatus after use.

Preferably, the open end of the body incorporates a generally cylindrical neck portion adjacent the rim, the outer surface of which is adapted to receive an extended elastic band. In this configuration, the band can be manually slid from the end of the neck and positioned adjacent the base of the organ at the appropriate time with the apparatus substantially in place, so as to restrict the outflow of blood and maintain the organ in the distended condition once the vacuum chamber is vented to atmosphere and the apparatus released.

In the preferred embodiment, the apparatus further includes an outer collar or transfer ring slidably disposed on the tubular body to facilitate transfer of the elastic band onto the organ.

The tubular body is preferably transparent to permit the condition of the male organ to be viewed during operation of the apparatus, to ensure that correct distension is achieved prior to the application of the elastic band and the subsequent relief of vacuum pressure within the chamber.

The above and other features of the invention including various and novel details of construction and combinations of parts will now be more particularly described with reference to the accompanying drawings and pointed out in the claims. It will be understood that the particular apparatus for obtaining an artificial erection embodying the invention is shown by way of illustration only and not as a limitation of the invention. The principles and features of this invention may be employed in varied and numerous embodiments without departing from the scope of the invention.

A preferred embodiment of the invention will now be described, by way of example only, with reference to the accompanying drawings.

BRIEF DESCRIPTION OF THE DRAWINGS

FIG. 1 is a side elevation showing an apparatus for obtaining an artificial erection according to the invention.

FIG. 2 is a left-hand end view of the apparatus of FIG. 1 showing the open end of the tubular body.

FIG. 3 is a right-hand end view of the apparatus of FIG. 1 showing the closed end of the body.

DETAILED DESCRIPTION

Figure 4:
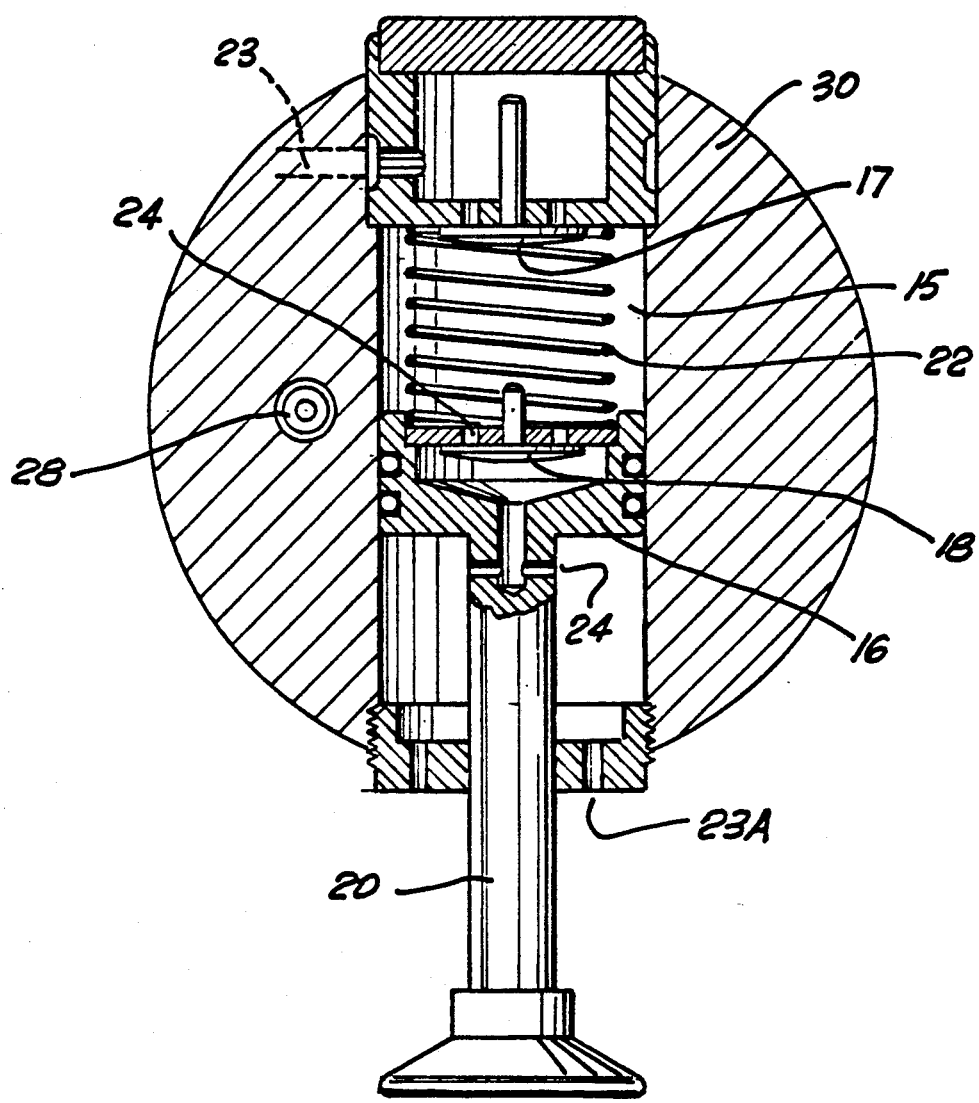
FIG. 4 is an enlarged cut away sectional view showing the pump and valve assembly.

Referring to the drawings, wherein correspond features are denoted by corresponding reference numerals, the invention provides an apparatus 1 for obtaining an artificial erection of the male genital organ (not shown).

The apparatus includes an elongate tubular body 2 partially defining a vacuum chamber 3 adapted to accommodate the male organ in an erect or distended condition. The body includes an opening 4 at one end to receive the organ and a continuous annular peripheral rim 5 surrounding the opening to substantially seal the vacuum chamber 3 around the organ, against the body of the user. The open end of the body further incorporates a generally cylindrical neck portion 7 adjacent the rim, the outer surface of which is adapted to slidably receive an extended elastic band (not shown). A transfer ring 8 is slidably disposed on the tubular body to facilitate transfer of the elastic band from the neck portion of the body onto the distended organ, as described in more detail below. A reduction insert 9 allows the effective inner diameter of the vacuum chamber to be reduced if necessary.

The other end of the body is substantially closed and incorporates a manually operable pump mechanism 10 adapted selectively and progressively to evacuate the vacuum chamber 3. The pump 10 comprises a pressure cylinder 15, a piston 16 manually reciprocable within the cylinder, and a cooperating pair of pressure actuable one-way flap valves 17 and 18 respectively associated with the cylinder 15 and the piston 16. The piston includes a manually operable plunger 20 protruding outwardly from the cylinder, and resilient bias means in the form of a compression spring 22 disposed within the cylinder. The spring is disposed resiliently to urge the piston toward a rest position corresponding to the end of a suction stroke. In this position, the plunger protrudes to a maximum extent from the cylinder.

The pressure actuable one-way flap valves 17 and 18 are disposed such that outward axial displacement of the piston 16 by the compression spring 22 in a direction corresponding to the suction stroke of the pump draws a corresponding volume of air into the pressure cylinder 15 from the vacuum chamber 3 through passage 23. It should be appreciated that for ease of illustration, passage 23 is shown rotated through 90° in FIG. 4. At the same time, air behind the piston from the previous stroke is exhausted through ports 23A. Displacement of the piston in the opposite direction in a return stroke by manual depression of the plunger 20 against the bias force of the spring allows the air within the pressure cylinder to pass the piston through vents 24 while the vacuum chamber is isolated by valve 17. The pumping cycle is thus repeated until the chamber has been evacuated to the required vacuum pressure. Accordingly, each suction stroke is effected automatically by the spring, and each return stroke is alternately effected manually by depression of the plunger, against the bias force of the spring. In this way, it will be appreciated that the maximum extent to which the vacuum chamber is evacuated by the pump is normally limited by the maximum compressive bias force of the spring. This provides an inherent safety feature, limiting the maximum vacuum pressure which can be applied.

Ideally, the maximum vacuum pressure required to achieve satisfactory results is around 40 cm mercury vacuum, and the spring is designed to produce this without injury by automatically limiting the piston stroke as the optimum pressure is approached. However, if necessary, the vacuum pressure may be further increased by manually withdrawing the piston to produce a full suction stroke.

Figure 5:
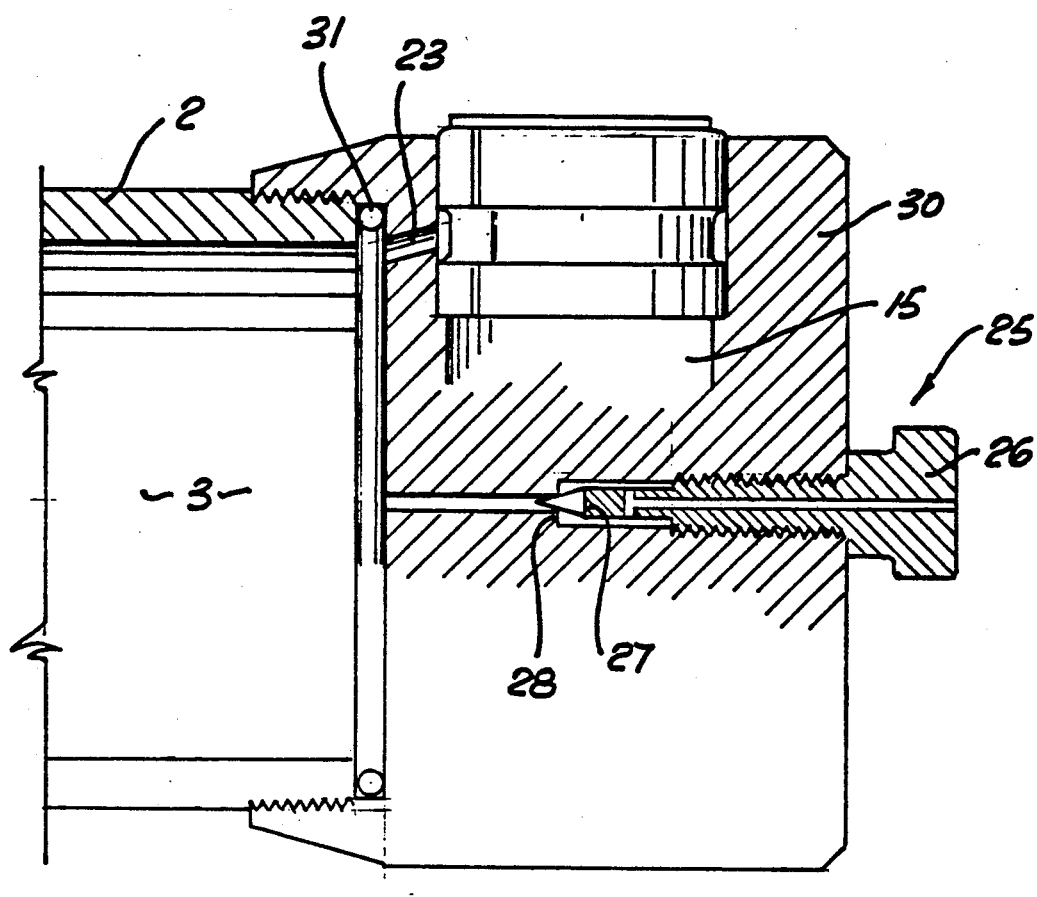
FIG. 5 is an enlarged cut away sectional view showing the pressure relief valve.

Pressure is released by manually operable relief valve assembly 25, which is best seen in FIG. 5. It will be apparent that counterclockwise rotation of the valve member 26 withdraws needle 27 from sealing engagement with complementary valve seat 28 to vent the vacuum chamber to atmosphere.

As best seen in FIGS. 4 and 5, the pump mechanism and relief valve assembly are housed within an end closure element 30 which is threadedly engageable with a complementary threaded portion formed on the corresponding end of the tubular body. An intermediate O-ring 31 ensures that a proper seal is maintained. The closure element thus defines a removable substantially closed end wall of the vacuum chamber, such that the pump is effectively integral with the assembled apparatus. The co-linear piston and cylinder axes extend transversely with respect to the longitudinal axis of the tubular body, to minimize the size of the apparatus and facilitate manual operation of the pump.

Turning now to describe the operation of the device, the hand pump is first attached to the threaded end section of the tubular body, ensuring that the rubber O-ring is properly seated. The pressure relief valve is closed by tightening into the body of the pump. Next, the transfer ring 8 is positioned onto the body, with the larger diameter end facing the pump. If necessary, a reduction insert 9 is fitted into the open end of the cylindrical body to reduce the effective diameter of the vacuum chamber. An elastic ring or band is fitted around the neck of the body, adjacent the open end of the apparatus. A suitable lubricant is then applied to the inside of the vacuum chamber particularly around the sealing rim, as well as to the elastic band. Once this initial set up procedure is completed, the genital organ is inserted into the open end of the tube and the apparatus pressed lightly against the body of the user such that the peripheral rim 5 seals the open end of the vacuum chamber around the organ. With the apparatus thus in position, the plunger of the pump is alternately depressed and released. During each suction stroke, as the plunger is pushed outwardly automatically by the spring, the one-way cylinder valve 17 opens while the cooperating piston valve closes such that air is progressively drawn into the cylinder from within the vacuum chamber through passage 23. Each return stroke is effected manually by depression of the plunger as previously described, whereby cylinder valve 17 is closed to isolate the vacuum chamber, and cooperating piston valve 18 is opened to exhaust the air from within the pressure cylinder past the piston to atmosphere through vents 24. This pumping cycle is repeated a number of times until the resultant vacuum pressure within the chamber causes blood to flow into the erectile tissue of the organ so as to induce an erection.

At the appropriate time, the elastic band (not shown) extended around cylindrical neck 7 is slid along the neck of the tube using the transfer ring 8, over the rim and positioned adjacent the base of the organ with the apparatus substantially in place. This restricts the outflow of blood and so maintains the organ in the distended condition. The vacuum chamber is then vented to atmosphere if necessary by manual operation of pressure relief valve 25 to release the apparatus.

In the preferred embodiment, the tubular body is fabricated from a substantially transparent plastic material to permit th condition of the organ to be viewed during the operation of the apparatus. This ensures that correct distension is achieved prior to the application of the elastic band.

Equivalents

Although the invention has been described with reference to a specific example, it will be appreciated by those skilled in the art that the invention may be embodied in many other forms.

I claim:

1. An apparatus for obtaining an artificial erection of the male genital organ, said apparatus including an elongate generally tubular body partially defining a vacuum chamber adapted to accommodate said organ in a distended condition, said tubular body having an opening at one end to receive the organ and a substantially continuous peripheral rim adjacent said opening to seal the vacuum chamber around the organ, the other end of the body being substantially closed and including manually operable pump means adapted selectively and progressively to evacuate said vacuum chamber such that, in use, the resultant differential pressure causes blood to flow into the organ and induce an artificial erection;

said pump means comprising a pressure cylinder, a piston manually reciprocable within the cylinder, and a cooperating pair of pressure actuable one way valves respectively associated with the cylinder and piston, the valves being disposed such that axial displacement of the piston in a first direction corresponding to a suction stroke of the pump draws a corresponding volume of air into the cylinder from within the vacuum chamber, and displacement of the piston in the opposite direction corresponding to a return stroke exhausts the air from within the cylinder while isolating the vacuum chamber;

the pump including a manually operable plunger connected with the piston and protruding outwardly from the cylinder, the resilient bias means disposed to urge the piston toward a rest position corresponding to the end of the suction stroke;

said resilient bias means comprising a compression spring disposed within the cylinder; and the pump being configured such that each suction stroke is affected automatically by the spring, and each return stroke is effected manually by the plunger against the bias force of the spring, whereby the maximum extent to which the vacuum chamber is evacuated tends to be limited by the maximum bias force of the spring.

2. An apparatus for obtaining an artificial erection of the male genital organ, said apparatus including an elongate generally tubular body partially defining a vacuum chamber adapted to accommodate said organ in a distended condition, said tubular body having an opening at one end to receive the organ and a substantially continuous peripheral rim adjacent said opening to seal the vacuum chamber around the organ, the other end of the body being substantially closed and including manually operable pump means adapted selectively and progressively to evacuate said vacuum chamber such that, in use, the resultant differential pressure causes blood to flow into the organ and induce an artificial erection;

said pump means comprising a pressure cylinder, a piston manually reciprocable within the cylinder, and a cooperating pair of pressure actuable one way valves respectively associated with the cylinder and piston, the valves being disposed such that axial displacement of the piston in a first direction corresponding to a suction stroke of the pump draws a corresponding volume of air into the cylinder from within the vacuum chamber, and displacement of the piston in the opposite direction corresponding to a return stroke exhausts the air from with the cylinder while isolating the vacuum chamber;

the pump including a manually operable plunger connected with the piston and protruding outwardly from the cylinder, the resilient bias means disposed to urge the piston toward a rest position corresponding to the end of the suction stroke;

said resilient bias means comprising a compression spring disposed within the cylinder;

the pump being configured such that each suction stroke is affected automatically by the spring, and each return stroke is effected manually by the plunger against the bias force of the spring, whereby the maximum extent to which the vacuum chamber is evacuated tends to be limited by the maximum bias force of the spring; and the spring being adapted to produce a maximum vacuum pressure within the vacuum chamber corresponding to between 20 cm and around 50 cm of mercury.

3. An apparatus for obtaining an artificial erection of the male genital organ, said apparatus including an elongate generally tubular body partially defining a vacuum chamber adapted to accommodate said organ in a distended condition, said tubular body having an opening at one end to receive the organ and a substantially continuous peripheral rim adjacent said opening to seal the vacuum chamber around the organ, the other end of the body being substantially closed and including manually operable pump means adapted selectively and progressively to evacuate said vacuum chamber such that, in use, the resultant differential pressure causes blood to flow into the organ and induce an artificial erection;

said pump means comprising a pressure cylinder, a piston manually reciprocable within the cylinder, and a cooperating pair of pressure actuable one way valves respectively associated with the cylinder and piston, the valves being disposed such that axial displacement of the piston in a first direction corresponding to a suction stroke of the pump draws a corresponding volume of air into the cylinder from within the vacuum chamber, and displacement of the piston in the opposite direction corresponding to a return stroke exhausts the air from within the cylinder while isolating the vacuum chamber;

the pump including a manually operable plunger connected with the piston and protruding outwardly from the cylinder, the resilient bias means disposed to urge the piston toward a rest position corresponding to the end of the suction stroke;

said resilient bias means comprising a compression spring disposed within the cylinder;

the pump being configured such that each suction stroke is affected automatically by the spring, and each return stroke is effected manually by the plunger against the bias force of the spring, whereby the maximum extent to which the vacuum chamber is evacuated tends to be limited by the maximum bias force of the spring;

the spring being adapted to produce a maximum vacuum pressure within the vacuum chamber corresponding to between 20 cm and around 50 cm of mercury; and the spring being designed to produce a maximum vacuum pressure within the vacuum chamber corresponding to around 40 cm of mercury.

* * * * *